(12) United States Patent
Cassidy et al.

(10) Patent No.: US 6,645,218 B1
(45) Date of Patent: Nov. 11, 2003

(54) SURGICAL INSTRUMENT

(75) Inventors: Stephen T. Cassidy, Greenville, RI (US); Ian K. Parker, Bristol, RI (US); Alan E. Shluzas, Millis, MA (US)

(73) Assignee: Endius Incorporated, Plainville, MA (US)

( * ) Notice: Subject to any disclaimer, the term of this patent is extended or adjusted under 35 U.S.C. 154(b) by 0 days.

(21) Appl. No.: 10/212,988

(22) Filed: Aug. 5, 2002

(51) Int. Cl.⁷ ............................................. A61B 17/32
(52) U.S. Cl. ...................................................... 606/170
(58) Field of Search ................................. 606/167, 170, 606/174, 180, 205–208

(56) References Cited

U.S. PATENT DOCUMENTS

| | | | | |
|---|---|---|---|---|
| 4,834,069 A | * | 5/1989 | Umeda ........................ | 600/142 |
| 5,178,129 A | * | 1/1993 | Chikama et al. ............. | 600/142 |
| 5,411,514 A | | 5/1995 | Fucci et al. | |
| 5,540,706 A | * | 7/1996 | Aust et al. ................... | 606/170 |
| 5,618,294 A | | 4/1997 | Aust et al. | |
| 5,669,926 A | * | 9/1997 | Aust et al. ................... | 606/170 |
| 5,851,212 A | * | 12/1998 | Zirps et al. .................. | 606/167 |
| 5,921,956 A | * | 7/1999 | Grinberg et al. ............ | 604/95.01 |
| 6,048,339 A | * | 4/2000 | Zirps et al. .................. | 604/525 |
| 6,461,453 B1 | * | 10/2002 | Abrams et al. .............. | 148/402 |
| 6,491,626 B1 | | 12/2002 | Stone et al. | |

* cited by examiner

Primary Examiner—Michael J. Milano
Assistant Examiner—Nguyen Victor
(74) Attorney, Agent, or Firm—Tarolli, Sundheim, Covell & Tummino L.L.P.

(57) ABSTRACT

A surgical instrument (10) includes a handle (12) and a member (30) for acting on tissue of a patient. A flexible stem (20) extends between the member (30) and the handle (12). The flexible stem (20) includes a tubular member (60) having a longitudinal axis (70) and radially inner and outer cylindrical surfaces (62 and 64) extending generally parallel to each other. The tubular member (60) has wedge-shaped slots (80 and 90) extending through the inner and outer cylindrical surfaces (62 and 64). Each of the wedge-shaped slots (80 and 90) is defined by first and second ring portions (92 and 94) extending at an angle to each other and transverse to the longitudinal axis (70). An actuator mechanism (14) connected with the handle (12) bends the flexible stem (20).

18 Claims, 3 Drawing Sheets

SURGICAL INSTRUMENT

TECHNICAL FIELD

The present invention relates to a surgical instrument and, more particularly, to a steerable endoscopic surgical instrument which may be used for cutting and/or removal of tissue.

BACKGROUND OF THE INVENTION

A known surgical instrument is disclosed in U.S. Pat. No. 5,540,706. U.S. Pat. No. 5,540,706 discloses a surgical instrument with a tubular articulated section extending between a handle and a member for acting on tissue. An actuator mechanism is connected with the handle and is operable to bend the articulated section.

SUMMARY OF THE INVENTION

The present invention is a surgical instrument including a handle and a member for acting on tissue of a patient. A flexible stem extends between the member and the handle. The flexible stem includes a tubular member having a longitudinal axis and radially inner and outer cylindrical surfaces extending generally parallel to each other. The tubular member has wedge-shaped slots extending through the inner and outer cylindrical surfaces. Each of the wedge-shaped slots are defined by first and second ring portions extending at an angle to each other and transverse to the longitudinal axis. An actuator mechanism connected with the handle bends the flexible stem.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein.

DESCRIPTION OF THE INVENTION

Figure 1:
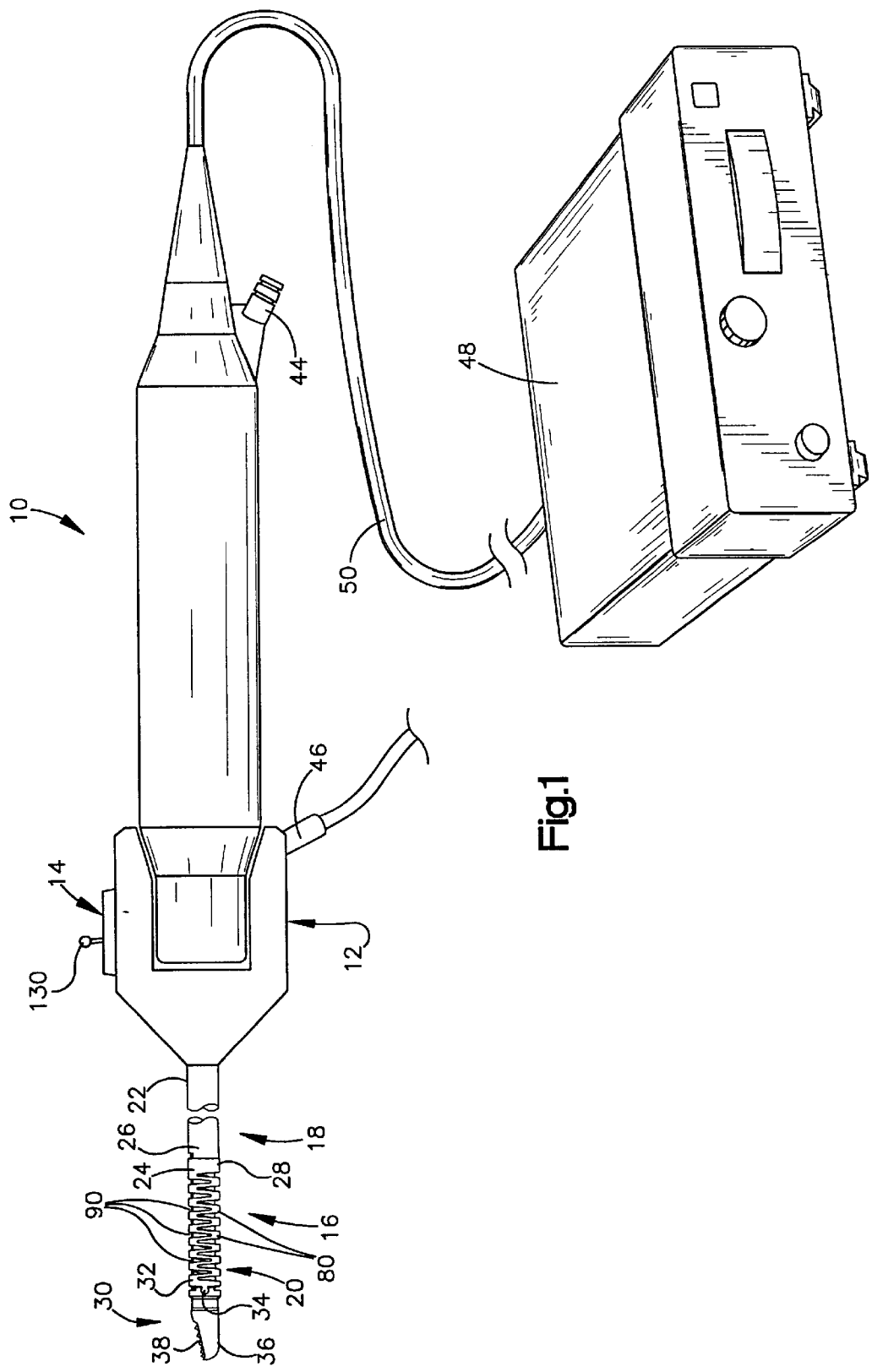
FIG. 1 is a schematic illustration of a surgical instrument constructed in accordance with the present invention.

The present invention relates to a surgical instrument and, in particular, to a steerable endoscopic surgical instrument which may be used for cutting and/or removal of tissue. As representative of the present invention, FIG. 1 illustrates a surgical instrument 10. The surgical instrument 10 includes a handle 12 and an actuator mechanism 14 connected with the handle. A stem section 16 is connected with and projects from the handle 12. The stem section 16 includes a first stem section or rigid stem section 18 and second stem section or flexible stem section 20. The actuator mechanism 14 bends the flexible stem section 20 as described below.

A proximal end portion 22 of the rigid stem section 18 is fixed to the handle 12. A proximal end portion 24 of the flexible stem section 20 is rigidly connected with a distal end portion 26 of the rigid stem section 18 by a soldered lap joint connection 28. The flexible stem section 20 may be rigidly connected to the rigid stem section 18 in any suitable manner. A rotary cutter assembly or shaver assembly 30 is pivotally connected with a distal end portion 32 of the flexible stem section 20 by a pivot connection 34. The shaver assembly 30 may be pivotally connected to the flexible stem section 20 in any suitable manner.

The shaver assembly 30 includes a fixed outer member 36 and a rotatable inner member 38. The outer member 36 (FIG. 2) of the shaver assembly 30 has a generally cylindrical, tubular configuration with a first cutting edge 40. The inner member 38 of the shaver assembly 30 has a generally cylindrical configuration and is rotatable within the outer member 36 of the shaver assembly. The inner member 38 of the shaver assembly 30 has a second cutting edge 42. Although a shaver assembly 30 is shown connected with the distal end 32 of the flexible stem section 20, it is contemplated that any member for acting on tissue of a patient could be connected with the distal end of the flexible stem section.

A suction pump (not shown) is connected with the handle 12 (FIG. 1) at a connection indicated at 44. A source of water or other irrigation fluid (not shown) is connected with the handle 12 at a connection 46. A control apparatus 48 is connected with the surgical instrument 10 through a cord system 50.

The rigid stem section 18 (FIG. 2) is substantially non-bendable during use of the surgical instrument 10. The rigid stem section 18 has a tubular cylindrical configuration including parallel inner and outer surfaces 52 and 54. The inner surface 52 defines a cylindrical central passage 56. The rigid stem section 18 has a longitudinal central axis 58 which forms a longitudinal central axis of the surgical instrument 10.

The flexible stem section 20 (FIG. 2) of the surgical instrument 10 includes an outer tubular member 60 for supporting the non-rotating outer member 36 of the shaver assembly 30 on the rigid stem section 18 of the surgical instrument. It is contemplated that the tubular member is made of Nitinol and is superelastic at approximately 60–65 ksi. The tubular member 60 has cylindrical radially inner and outer surfaces 62 and 64 that extend parallel to each other. The inner surface 62 defines a cylindrical central passage 68 which is a continuation of the passage 56 in the rigid stem section 18. The passages 56 and 68 provide a path for irrigation fluid. The tubular member 60 has a longitudinal axis 70 that is a continuation of the axis 58.

A first plurality of wedge-shaped slots 80 extend through the inner and outer cylindrical surfaces 62 and 64 and transverse to the longitudinal axis 70. The wedge-shaped slots 80 extend from a lower side, as viewed in FIG. 2, of the longitudinal axis 70 of the flexible stem section 20 toward the longitudinal axis. A second plurality of wedge-shaped slots 90 extend through the inner and outer cylindrical surfaces 62 and 64 and transverse to the longitudinal axis 70. The wedge-shaped slots 90 extend from an upper side, as viewed in FIG. 2, of the longitudinal axis 70 toward the longitudinal axis. There are nine wedge-shaped slots 80 and eight wedge-shaped slots 90 shown in FIG. 2. It is contemplated that any number of wedge-shaped slots 80 and 90 may be formed in the flexible stem section 20 depending on the length of the flexible stem section.

Each of the wedge-shaped slots 90 is axially located between the wedge-shaped slots 80. The wedge-shaped slots 80 and 90 are defined by ring portions 92 and 94 extending at an angle to each other and transverse to the longitudinal axis 70. Each of the ring portions 94 is axially located between the ring portions 92. The ring portions 92 and 94 extend at an angle of approximately 10° to each other. The ring portions 92 extend generally parallel to each other and the ring portions 94 extend generally parallel to each other.

Figure 2:
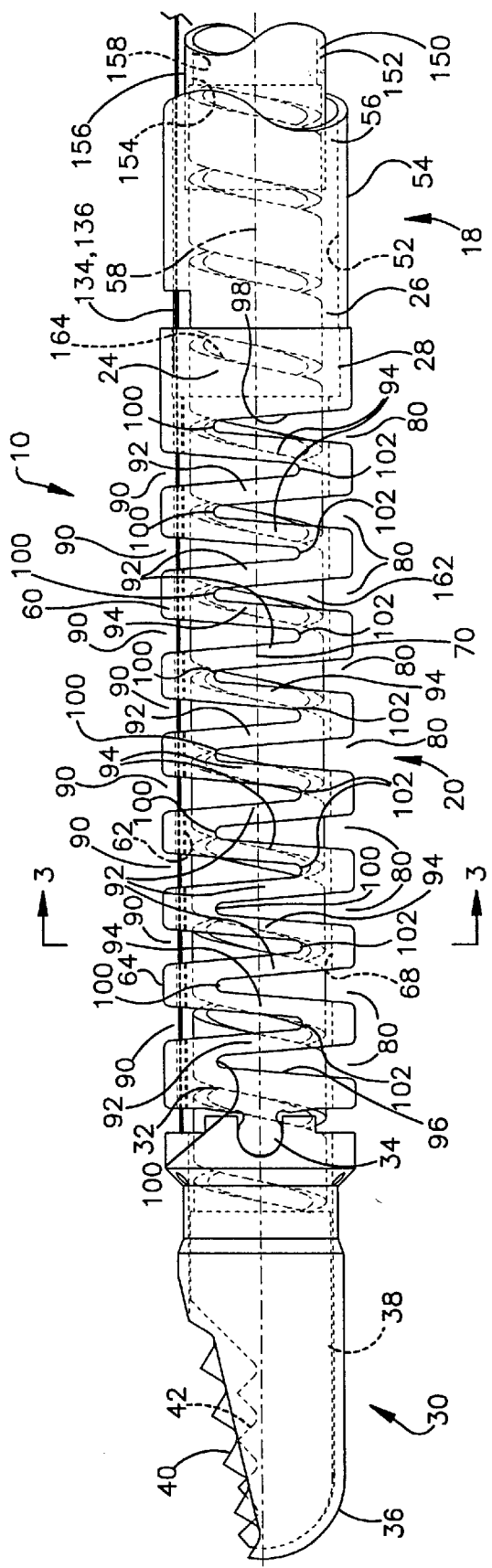
FIG. 2 is an enlarged schematic view of a stem of the surgical instrument of FIG. 1.

The ring portions 92 and 94 are interconnected to define apexes 100 of the slots 80 located on the upper side, as viewed in FIG. 2, of the longitudinal axis 70. The ring portions 92 and 94 diverge away from each other toward the outer surface 64 located on the lower side of the axis 70. Accordingly, the wedge-shaped slots 80 extend radially from the cylindrical outer surface 64 on the lower side of the longitudinal axis 70 to an opposite or upper side of the longitudinal axis. The ring portions 92 and 94 are also interconnected to define apexes 102 of the slots 90 located on the lower side of the longitudinal axis 70. The ring portions 92 and 94 diverge away from each other toward the cylindrical outer surface 64 located on the upper side of the axis 70. Accordingly, the wedge-shaped slots 90 extend radially from the cylindrical outer surface 64 on an upper side of the longitudinal axis to a lower side of the longitudinal axis. Furthermore, each wedge-shaped slot 80 is defined by first and second ring portions 92 and 94 extending at an angle to each other. The wedge-shaped slot 90 located axially adjacent to the slot 80 is defined by the second ring portion 94 and a third ring portion 92 extending from the second ring portion 94.

The slot 80 located adjacent the distal end 32 of the stem section 20 is defined by the end 32 and ring portion 92 extending from the end 32. The end 32 has a surface 96 extending at an angle of approximately 10° to the ring portion 92 extending from the end 32. The slot 80 located adjacent the proximal end 24 of the stem section 20 is defined by the end 24 and ring portion 94 extending from the end 24. The end 24 has a surface 98 extending at an angle of approximately 10° to the ring portion 94 extending from the end 24.

A pair of cylindrical deflection control wire passages 110 and 112 (FIG. 3) are formed in the inner surface 62 of the tubular member 60. The passages 110 and 112 extend parallel to each other and to the axis 70. The passages 110 and 112 extend along the length of the flexible stem section 20 and on the upper side of the longitudinal axis 70, as viewed in FIG. 3.

Figure 3:
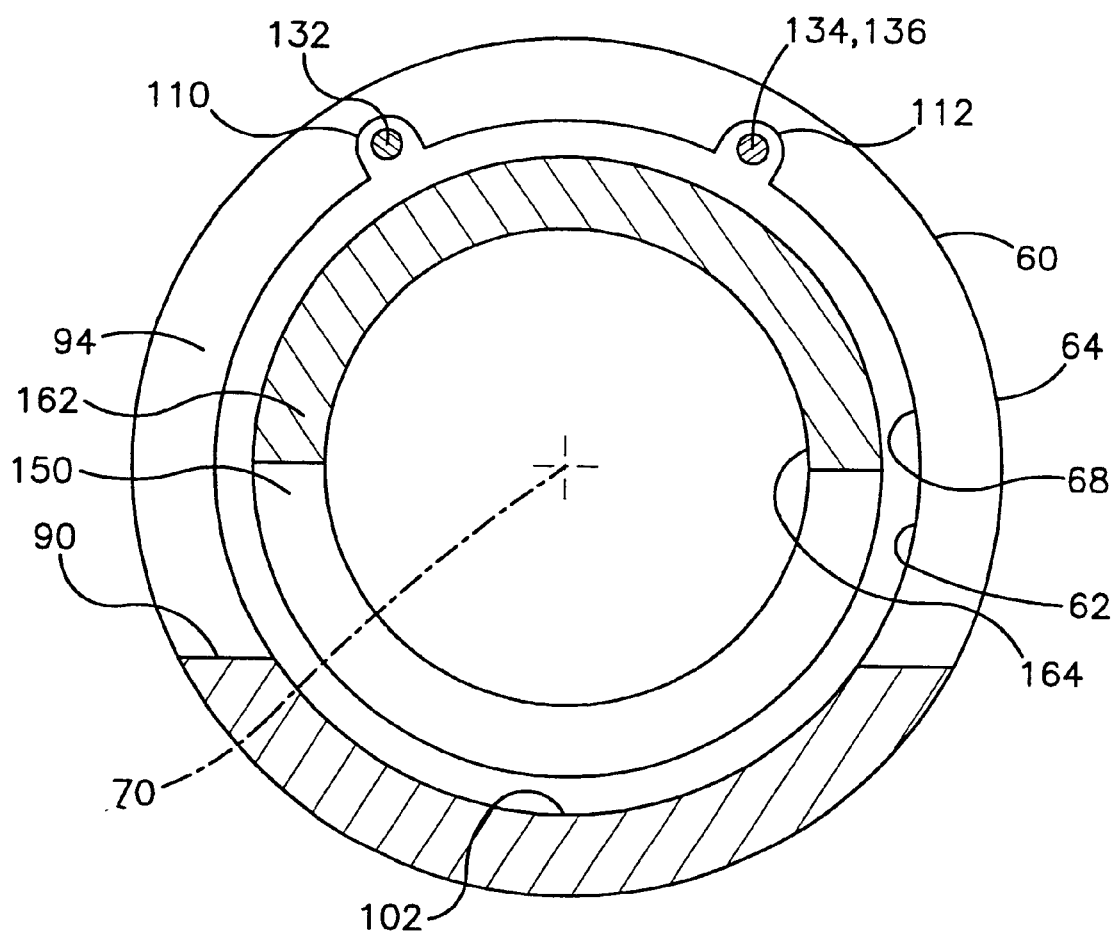
FIG. 3 is a schematic sectional view taken along line 3—3 of FIG. 2.

The actuator assembly 14 (FIG. 1) of the surgical instrument 10 includes a deflection control lever 130 which projects from the handle 12. The deflection control lever 130 is supported for pivotal movement relative to the handle 12. The actuator assembly 14 includes at least two elongate flexible members or deflection control wires 132 and 134 (FIG. 3). The wires 132 and 134 are separate portions of a single loop of wire 136 which has its proximal ends connected for movement with the deflection control lever 130. The deflection control wires 132 and 134 are made from a superelastic metal alloy which limits stress on the actuator assembly 14.

The deflection control wires 132 and 134 extend from the deflection control lever 130 through the deflection control wire passages 110 and 112, respectively, in the tubular member 60. The deflection control wires 132 and 134 are connected in a known manner in a force-transmitting relationship with the fixed portion 36 of the shaver assembly 30. It is contemplated that the control wires 132 and 134 loop around a fixed portion of the shaver assembly 30. As a result, tensile forces on the control wires 132 and 134, resulting from movement of the actuator control lever 130, are transmitted to the shaver assembly 30 to bend the flexible stem section 20.

A rotatable drive shaft 150 (FIGS. 2 and 3) is disposed radially inward of the tubular member 60 of the surgical instrument 10. A rigid portion 152 (FIG. 2) of the drive shaft 150 is disposed within the rigid stem section 18. The rigid portion 152 of the drive shaft 150 is a cylindrical metal tube which has parallel cylindrical inner and outer surfaces 154 and 156. The inner surface 154 of the rigid portion 152 of the drive shaft 150 defines a central passage 158. The rigid portion 152 of the drive shaft 150 is connected with the drive shaft (not shown) of a suitable electric motor in the handle 12 and is rotatable about the longitudinal central axis 58 by operation of the motor.

A flexible tubular portion 162 of the drive shaft 150 is disposed within the flexible stem section 20. It is contemplated that the flexible portion 162 of the drive shaft 150 could be formed of a helical coil spring or a flexible tubular polymer. The flexible portion 162 of the drive shaft 150 is capable of transmitting rotational force from the rigid portion 152 of the drive shaft 150 to the rotatable inner part 38 of the shaver assembly 30. The flexible portion 162 of the drive shaft 150 has an axially extending central passage 164. The passages 158 and 164 in the drive shaft 150 provide a suction path for tissue and fluid evacuation.

When the actuation control lever 130 is pivoted relative to the handle 12, so as to tension the deflection control wires 132 and 134, tension in the wires is effective to bend the flexible stem section 20. The flexible stem section 20 bends in an upward direction, as viewed in FIGS. 1 and 2, extending parallel to the direction in which the slots 90 extend through the inner and outer surfaces 62 and 64 and transverse to the axis 70. The flexible stem section 20 is prevented from bending in any direction extending transverse to the upward direction. The shaver assembly 30 is pulled from an unactuated linear position, shown in FIGS. 1 and 2. The actuator assembly 14 can thus be operated to change the orientation of the shaver assembly 30 relative to the rigid stem section 18 and relative to body tissue during an operation. The actuator assembly 14 can be operated to positively change the orientation of the shaver assembly 30 from the straight initial orientation. The drive shaft 150 and the inner shaver part 38 are rotatable to effect tissue removal while the flexible stem section 20 is in any orientation. The superelasticity of the tubular member 60 and the flexible portion 162 of the drive shaft 150 return the flexible stem section to the unactuated linear position.

From the above description of the invention, those skilled in the art will perceive improvements, changes and modifications. Such improvements, changes and modifications within the skill of the art are intended to be covered by the appended claims.

Having described the invention, the following is claimed:

1. A surgical instrument comprising:

a handle;

a member for acting on tissue of a patient;

a flexible stem extending between said member and said handle, said flexible stem having an unactuated linear position, said flexible stem including a tubular member having a longitudinal axis and radially inner and outer cylindrical surfaces extending generally parallel to each other, said tubular member having wedge-shaped slots extending through said inner and outer cylindrical surfaces when said flexible stem is in said unactuated linear position, each of said wedge-shaped slots being defined by first and second ring portions extending at an angle to each other and transverse to said longitudinal axis, a first wedge-shaped slot extending radially from said cylindrical outer surface on one side of said longitudinal axis toward said longitudinal axis and a second wedge-shaped slot extending radially from said cylindrical outer surface on an opposite side of said longitudinal axis toward said longitudinal axis; and an actuator mechanism connected with said handle for bending said flexible stem.

2. A surgical instrument as set forth in claim 1 wherein said first wedge-shaped slot is defined by said first and second ring portions extending at an angle to each other when said flexible stem is in said unactuated linear position, said second wedge-shaped slot being defined by said second ring portion and a third ring portion extending at an angle to said second ring portion when said flexible stem is in said unactuated linear position.

3. A surgical instrument as set forth in claim 2 wherein said first ring portion extends generally parallel to said third ring portion when said flexible stem is in said unactuated linear position.

4. A surgical instrument as set forth in claim 1 wherein said first wedge-shaped slot extends radially from said cylindrical outer surface on said one side of said longitudinal axis to an opposite side of said longitudinal axis.

5. A surgical instrument as set forth in claim 4 wherein said second wedge-shaped slot extends radially from said cylindrical outer surface on said opposite side of said longitudinal axis to said one side of said longitudinal axis.

6. A surgical instrument as set forth in claim 4 wherein said first and second ring portions are interconnected to define an apex of said first wedge-shaped slot, said apex being located on said opposite side of said longitudinal axis.

7. A surgical instrument as set forth in claim 1 wherein said first and second ring portions defining said slots extend at an angle of approximately 10° to each other when said flexible stem is in said unactuated linear position.

8. A surgical instrument as set forth in claim 1 wherein said flexible stem is rigidly connected with rigid stem extending between said handle and said flexible stem, said flexible stem being pivotally connected to said member for acting on tissue.

9. A surgical instrument as set forth in claim 1 wherein said flexible stem is superelastic at approximately 60–65 ksi.

10. A surgical instrument as set forth in claim 9 wherein said flexible stem is made of Nitinol.

11. A surgical instrument as set forth in claim 1 wherein said actuator mechanism includes at least one elongate flexible member extending through said flexible stem, said actuator mechanism including means for pulling on said at least one elongate flexible member to bend said flexible stem.

12. A surgical instrument as set forth in claim 11 wherein said flexible stem includes a passage through which said flexible member extends.

13. A surgical instrument as set forth in claim 12 wherein said flexible stem includes a radially inner passage formed in said inner cylindrical surface through which said flexible member extends.

14. A surgical instrument as set forth in claim 1 wherein said member for acting on tissue includes a drive shaft having a flexible portion extending through said flexible stem, said flexible portion of said drive shaft being rotatable about said longitudinal axis relative to said flexible stem.

15. A surgical instrument as set forth in claim 1 wherein said flexible stem is bendable from said unactuated position in a first direction extending parallel to the direction in which said wedge-shaped slots extend through said inner and outer cylindrical surfaces and transverse to said longitudinal axis, said flexible stem being prevented from bending in a direction extending transverse to said first direction.

16. A surgical instrument as set forth in claim 1 wherein said flexible stem includes a passage for irrigation fluid.

17. A surgical instrument as set forth in claim 1 wherein said flexible stem includes a passage for tissue evacuation.

18. A surgical instrument as set forth in claim 1 wherein said actuator mechanism includes at least one elongate flexible member made of a superelastic alloy to limit stress on said actuator mechanism.

* * * * *